US012776390B2

(12) United States Patent
Zheng et al.

(10) Patent No.: US 12,776,390 B2
(45) Date of Patent: Oct. 27, 2026

(54) METHOD FOR EVALUATING METALLOGENIC POTENTIAL OF SKARN DEPOSIT BASED ON MAGNETITE COMPOSITION

(71) Applicants: CHINA UNIVERSITY OF GEOSCIENCES (BEIJING), Beijing (CN); Tibet Julong Copper Co., Ltd., Lhasa (CN)

(72) Inventors: Youye Zheng, Beijing (CN); Lei Li, Beijing (CN); Xiaofang Dou, Beijing (CN); Zhixin Zhang, Lhasa (CN); Jinling Liao, Lhasa (CN); Qiong Ci, Lhasa (CN); Song Wu, Beijing (CN); Xiaofeng Liu, Lhasa (CN); Jingjing Li, Lhasa (CN); Peng Kang, Lhasa (CN)

(73) Assignees: CHINA UNIVERSITY OF GEOSCIENCES (BEIJING), Beijing (CN); Tibet Julong Copper Co., Ltd., Lhasa (CN)

( * ) Notice: Subject to any disclaimer, the term of this patent is extended or adjusted under 35 U.S.C. 154(b) by 440 days.

(21) Appl. No.: 18/491,811

(22) Filed: Oct. 23, 2023

(65) Prior Publication Data

US 2024/0290437 A1 Aug. 29, 2024

(30) Foreign Application Priority Data

Feb. 23, 2023 (CN) ......................... 202310184807.4

(51) Int. Cl.
*G16C 20/20* (2019.01)
*G01N 33/2028* (2019.01)
*G01N 33/24* (2006.01)

(52) U.S. Cl.
CPC ......... *G16C 20/20* (2019.02); *G01N 33/2028* (2019.01); *G01N 33/24* (2013.01)

(58) Field of Classification Search
CPC .... G16C 20/20; G01N 33/2028; G01N 33/24; G01N 27/626; G01V 3/38
See application file for complete search history.

(56) References Cited

U.S. PATENT DOCUMENTS 10,281,434 B2 5/2019 Lippert-gellissen et al.
11,378,563 B2 7/2022 Abedini
11,726,060 B2 8/2023 Calvo et al.

FOREIGN PATENT DOCUMENTS

CN 115078520 A * 9/2022 ............. G01N 27/64

OTHER PUBLICATIONS

English translation for CN-115078520-A (Year: 2022).*

* cited by examiner

*Primary Examiner* — Lee E Rodak
*Assistant Examiner* — Byung Ro Lee

(57) ABSTRACT

The present invention discloses a method for evaluating a metallogenic potential of a skarn deposit based on the magnetite composition, including collecting geological, geophysical, geochemical, and remote sensing data in a studying area, systematically, and delineating a favorable area for mineralization; collecting magnetite-bearing samples in the favorable area for mineralization, and describing the lithology, alteration and mineralization characteristics of each sample; selecting the most representative magnetite samples for chemical analysis to obtain average contents of trace elements Ti, Ni, V, K and Al+Si+Mg, denoted as c(Ti), c(Ni), c(V), c(K), and c(Al+Si+Mg) in ppm; and calculating discriminant factors F1, F2, F3, and F4 by substituting data, and performing discrimination; and when the four discriminant factors all discriminate the metallogenic potential to be better, determining the skarn deposit in the favorable area for mineralization to have a good metallogenic potential; and discriminating as a poor metallogenic potential in the remaining cases.

6 Claims, 2 Drawing Sheets

METHOD FOR EVALUATING METALLOGENIC POTENTIAL OF SKARN DEPOSIT BASED ON MAGNETITE COMPOSITION

CROSS-REFERENCE TO RELATED APPLICATIONS

This application claims priority to Chinese Patent Application No. 202310184807.4 with a filing date of Feb. 23, 2023. The content of the aforementioned application, including any intervening amendments thereto, is incorporated herein by reference.

TECHNICAL FIELD

The present invention belongs to the technical field of exploration, and in particular relates to a method for evaluating a metallogenic potential of a skarn deposit.

BACKGROUND

In the fragile ecological environment area of a plateau, the conventional exploration method is relatively costly and time-consuming, making it difficult to provide a clear exploration direction quickly. How to predict and evaluate a resource potential at a scale of an ore concentration area through limited exploration and evaluation techniques, guiding deposit exploration effectively, is the focus of domestic and foreign mineral exploration scientists.

Skarn deposits are mostly developed near contact zones between intermediate acidic magmatic rocks and carbonates. The occurrence and morphology of ore bodies are relatively complex, the continuity of the ore bodies is poor, the composition of minerals is complex, and the temperature range of formation is wide. During skarn formation, there is obvious zoning, with magnetite mostly formed in a late skarn stage and an oxide stage, and the formation temperature is relatively high. Skarn is developed in skarn deposits of different sizes, and how to quickly evaluate a metallogenic potential of this deposit (point) through the characteristics of skarn is a difficult point at present.

The conventional evaluation of a metallogenic potential of the skarn deposits requires to be based on large-scale geological mapping, geophysical and geochemical exploration work, and final drilling verification, and requires to complete mineral exploration stages such as general investigation and detailed investigation to evaluate the potential of the deposits, and has the following disadvantages: a long exploration and evaluation period, and a high cost, which cannot meet the urgent needs of rapid exploration and evaluation.

SUMMARY OF PRESENT INVENTION

An object of the present invention is to provide a new method for evaluating a metallogenic potential of a skarn deposit, which organically combines mineral geochemistry and deposit potential evaluation based on the differences in major and trace elements of magnetite in the skarn deposit, and solves the technical problem of rapid exploration and evaluation of skarn deposits in a plateau area.

To achieve the above object, the technical solutions adopted are as follows:

a method for evaluating a metallogenic potential of a skarn deposit based on the magnetite composition, including the steps of:

(1) Regional Data Collection and Comprehensive Analysis collecting geological, geophysical, geochemical, and remote sensing data in a studying area, systematically, and delineating a favorable area for mineralization;

(2) Magnetite Sample Collection collecting magnetite-bearing samples in the favorable area for mineralization by zoning, and describing the lithology, alteration and mineralization characteristics of each sample;

(3) Analysis of Major and Trace Elements in the Samples selecting the most representative magnetite samples for chemical analysis to obtain average contents of trace elements Ti, Ni, V, K and Al+Si+Mg, denoted as c(Ti), c(Ni), c(V), c(K), and c(Al+Si+Mg) in ppm; and (4) Discrimination of Evaluation of the Metallogenic Potential of the Deposit calculating a discriminant factor F1 by substituting c(Ni) into $F1=-3.1484*c(Ni)+13.301$, and when $c(V)>F1$, discriminating as a poor metallogenic potential, and otherwise, discriminating as a better metallogenic potential;

comparing c(V) with a discriminant factor F2=2, and when $c(V)>2$, discriminating as a poor metallogenic potential, and otherwise, discriminating as a better metallogenic potential;

calculating a discriminant factor F3 by substituting c(K) into $F3=0.0437*c(K)+0.4093$, and when $c(V)>F3$, discriminating as a poor metallogenic potential, and otherwise, discriminating as a better metallogenic potential;

calculating a discriminant factor F4 by substituting c(Ti) into $F4=-115.11*c(Ti)+34361$, and when $c(Al+Si+Mg)>F4$, discriminating as a poor metallogenic potential, and otherwise, discriminating as a better metallogenic potential; and when the four discriminant factors all discriminate the metallogenic potential to be better, determining the skarn deposit in the favorable area for mineralization to have a good metallogenic potential; and discriminating as a poor metallogenic potential in the remaining cases.

According to the above solution, the sample collecting process in the step 2 includes recording a drill hole number and a drill hole depth, taking a field picture, and making a detailed field record at each sample collecting position; wherein the number of the samples is not less than five.

According to the above solution, selecting the most representative magnetite samples in the step 3 includes:

grinding the collected samples into laser in-situ targets, observing the characteristics of magnetite corresponding to the collected samples under a microscope, recording the mineral associations and their magnetite morphology in detail, and selecting the most representative magnetite samples according to the results under the microscope.

According to the above solution, the chemical analysis in the step 3 includes:

performing in-situ micro-area elemental analysis by using laser ablation inductively coupled plasma mass spectrometry to obtain recorded data for each analytical point.

According to the above solution, the step 3 further includes processing the recorded data obtained from the chemical analysis by using data processing software, including:

① data importing, namely batch-importing elemental analysis recorded data obtained from in-situ micro-area analytical points of each magnetite sample into ICPMSDataCal software;

② data interpretation, namely obtaining an integral curve of micro-area elements in the samples at each observation point, and adjusting the start time and the end time of the integral curve for each observation point one by one according to a principle of ensuring that a signal range of the integral curve of the selected elements is the flattest and the widest;

③ data screening, namely rejecting invalid data according to an abnormal peak of the integral curve of the elements; and ④ data exporting, namely summarizing and batch-exporting interpreted and screened micro-area data for each single point into a file in a csv format.

According to the above solution, the discriminant factors F1, F2, F3, and F4 in the step 4 are obtained by a method including the following steps of:

(1) separately collecting magnetite-containing samples in an area where the skarn deposit is known to have a good metallogenic potential and an area where the skarn deposit is known to have a poor metallogenic potential;

(2) selecting the most representative magnetite samples for chemical analysis to obtain average contents of trace elements Ti, Ni, V, K and Al+Si+Mg, denoted as c(Ti), c(Ni), c(V), c(K), and c(Al+Si+Mg) in ppm; and (3) calculating the discriminant factors performing diagram projection on data of sample collecting points with c(Ni) as an abscissa and c(V) as an ordinate, and fitting a boundary of the good metallogenic potential and the poor metallogenic potential to calculate the discriminant factor F1: F1=−3.1484*c(Ni)+13.301;

performing diagram projection on data of sample collecting points with c(Ti) as an abscissa and c(V) as an ordinate, and fitting a boundary of the good metallogenic potential and the poor metallogenic potential to calculate the discriminant factor F2: F2=2;

performing diagram projection on data of sample collecting points with c(K) as an abscissa and c(V) as an ordinate, and fitting a boundary of the good metallogenic potential and the poor metallogenic potential to calculate the discriminant factor F3: F3=0.0437*c(K)+0.4093; and performing diagram projection on data of sample collecting points with c(Ti) as an abscissa and c(Al+Si+Mg) as an ordinate, and fitting a boundary of the good metallogenic potential and the poor metallogenic potential to calculate the discriminant factor F4: F4=−115.11*c(Ti)+34361.

Compared with the prior art, the beneficial effects of the present invention are as follows:

magnetite is a widely occurring mineral in magma and hydrothermal solution, and the formation of magnetite is not only influenced by crystallographic factors, but also controlled by changes in physical and chemical conditions. The temperature is one of the main factors controlling the composition of the magnetite. The present invention inventively proposes that the magnetite is used as a discriminating characteristic mineral to rapidly distinguish skarn with a larger metallogenic potential from skarn with a smaller metallogenic potential according to the change of major and trace elements of the magnetite, which is a new technical method for prospecting that is economical, efficient, and green, and can shorten the exploration and evaluation period, reduce exploration costs, and improve the exploration and evaluation efficiency, and meets the urgent needs of rapid exploration and evaluation of mining rights holders.

The present invention inventively proposes the use of trace elements of Ti, Ni, V and major elements of Al, K, Si and Mg in the magnetite, and inventively proposes the optimum discrimination ranges of the elements. The elements are sensitive to changes in temperature, water-rock interactions and redox conditions, and within the optimal discrimination ranges, accurate evaluation of the metallogenic potential of the skarn deposit can be made.

DETAILED DESCRIPTION OF THE EMBODIMENTS

The following embodiments further illustrate the technical solutions of the present invention, but are not intended to limit the scope of protection of the present invention.

Figure 1:
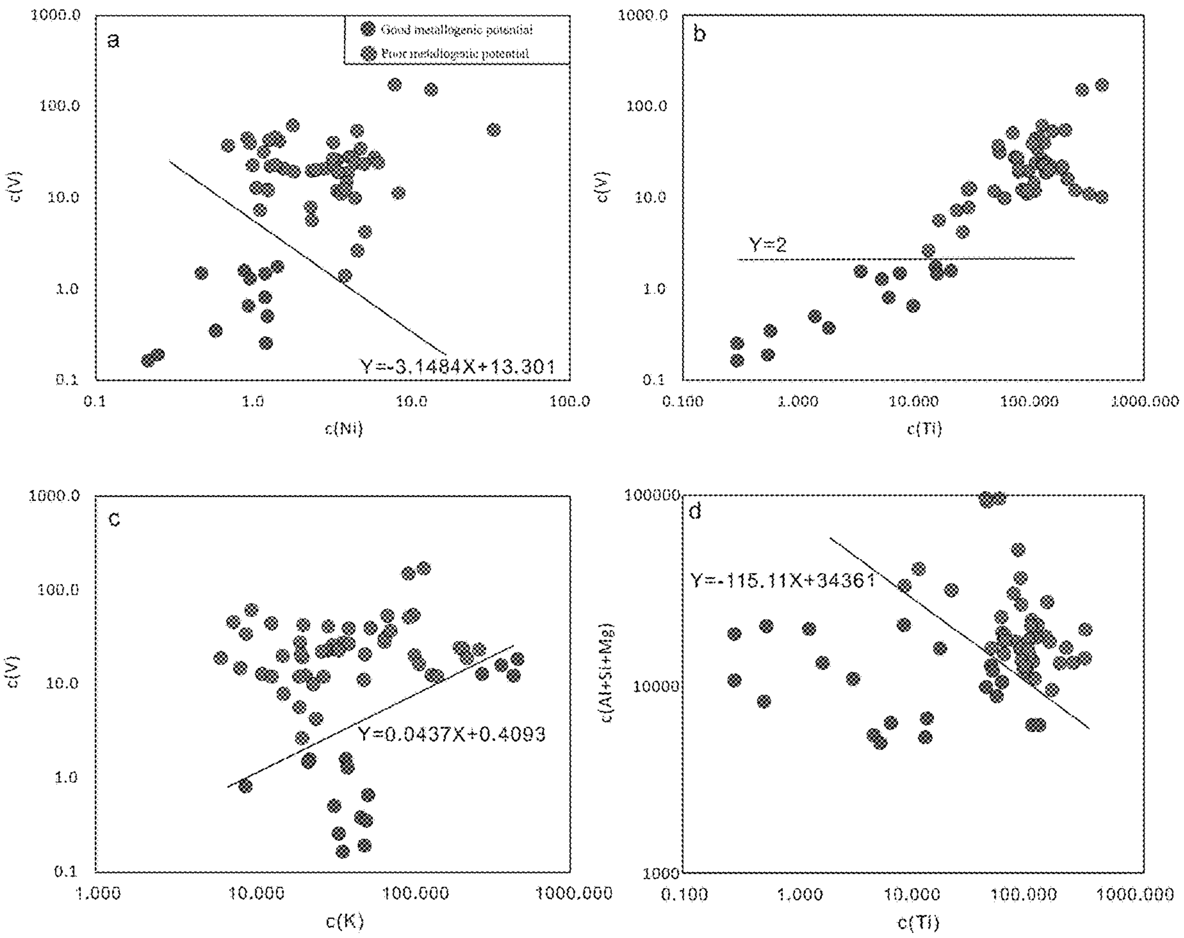
FIG. 1: a diagram showing discrimination of a metallogenic potential of a skarn deposit in Detailed Description.

A specific embodiment provides a process for obtaining discriminant factors F1, F2, F3, and F4 by using skarn deposits with a known metallogenic potential:

(1) magnetite-bearing samples are collected in an area where the skarn deposit is known to have a good metallogenic potential and an area where the skarn deposit is known to have a poor metallogenic potential, respectively;

(2) the most representative magnetite samples are selected for chemical analysis to obtain average contents of trace elements Ti, Ni, V, K and Al+Si+Mg, denoted as c(Ti), c(Ni), c(V), c(K), and c(Al+Si+Mg) in ppm; and (3) the discriminant factors F1, F2, F3, and F4 are calculated; wherein a, b, c, and d are fitting processes for the discriminant factors F1, F2, F3, and F4, respectively referring to FIG. 1;

diagram projection is performed on data of sample collecting points with c(Ni) as an abscissa and c(V) as an ordinate, and a boundary of the good metallogenic potential and the poor metallogenic potential is fitted to calculate the discriminant factor F1: F1=−3.1484*c(Ni)+13.301;

diagram projection is performed on data of sample collecting points with c(Ti) as an abscissa and c(V) as an ordinate, and a boundary of the good metallogenic potential and the poor metallogenic potential is fitted to calculate the discriminant factor F2: F2=2;

diagram projection is performed on data of sample collecting points with c(K) as an abscissa and c(V) as an ordinate, and fitting a boundary of the good metallogenic potential and the poor metallogenic potential is fitted to calculate the discriminant factor F3: F3-0.0437*c(K)+0.4093; and diagram projection is performed on data of sample collecting points with c(Ti) as an abscissa and c(Al+Si+Mg) as an ordinate, and fitting a boundary of the good metallogenic potential and the poor metallogenic potential is fitted to calculate the discriminant factor F4: F4=−115.11*c(Ti)+34361.

Figure 2:
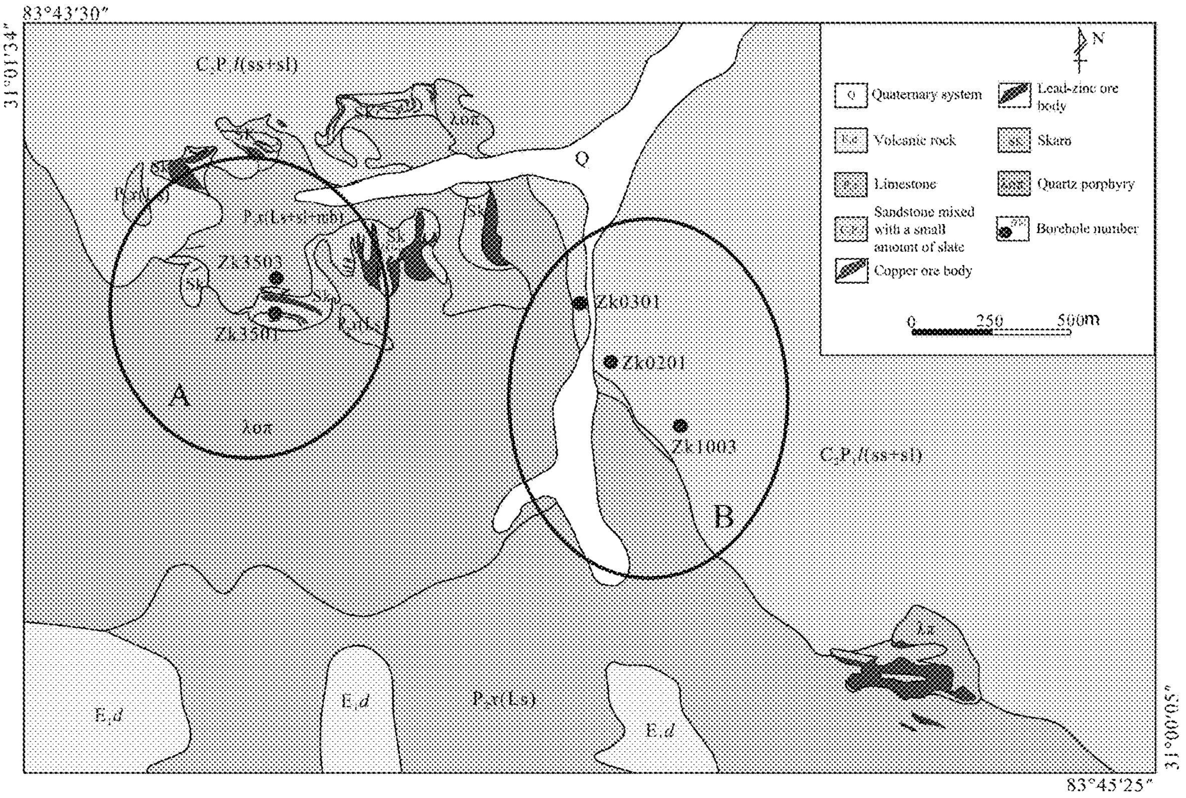
FIG. 2: a geological map showing sample collecting in a studying area in Detailed Description.

A specific embodiment also provides a process for discriminating skarn deposits with an unknown metallogenic potential:

a. geological, geophysical, geochemical, and remote sensing data in an ore concentration area is collected, systematically, and magnetite-bearing samples are collected in drill holes in two areas, respectively, and as shown in FIG. 2, the two areas are an area A and an area B, respectively.

b. Field sample collection

Magnetite samples are collected in 5 drill holes. During the sample collecting process, the following information is recorded truthfully in detail, as shown in Table 1.

TABLE 1

| Sample No. | Magnetite morphology | Lithology | Hand specimen alteration | Mineralization |
|---|---|---|---|---|
| Zk3503-174.6 | Idiomorphic | Actinolite skarn | Actinolitization | Galena mineralization, and sphalerite mineralization |
| Zk1003-524.7 | Veined | Chlorite skarn | Chloritization | Galena mineralization, and sphalerite mineralization |
| Zk0301-85.9 | Other shaped | Epidote skarn | Epidotization | No mineralization |
| . . . | . . . | . . . | . . . | . . . |

c. Sample analysis

The collected samples are ground into laser in-situ targets, the characteristics of magnetite corresponding to the collected samples are observed under a microscope, the mineral associations and their magnetite morphology (including an idiomorphic morphology or a veined morphology, etc.) are recorded in detail, the most representative magnetite samples are selected according to the results under the microscope, and marked with a marking pen, and in-situ micro-area elemental analysis by laser ablation inductively coupled plasma mass spectrometry (LA-ICPMS) is performed, wherein delineated areas are areas where magnetite develops, and the magnetite samples are subjected to in-situ analysis by LA-ICPMS, and the number of each analytical point is marked, and the in-situ analysis data is shown in Table 2 in ppm ($10^{-6}$).

TABLE 2

| | Ti | Al | Si | K | Mg | V | Ni |
|---|---|---|---|---|---|---|---|
| Area A | | | | | | | |
| 3503-179.1-1-2 | 60.467 | 1436.500 | 9733.066 | 68.260 | 1323 | 1.3 | 2.78 |
| 3503-179.1-1-1 | 68.137 | 511.454 | 7983.358 | 38.123 | 105 | 1.5 | 2.84 |
| 3503-179.1-2-1 | 54.535 | 459.804 | 7147.759 | 41.175 | 2016 | 1.2 | 1.38 |
| 3503-179.1-2-2 | 90.544 | 2236.533 | 28840.308 | 73.247 | 4639 | 1.10 | 1.50 |
| 3503-174.6-5 | 15.486 | 95.394 | 5088.362 | 0.000 | 32.9 | 1.06 | 1.41 |
| 3503-174.6-3 | 7.626 | 116.855 | 5947.653 | 0.000 | 143 | 1.49 | 0.47 |
| 3503-174.6-1 | 3.486 | 171.787 | 10192.266 | 22.590 | 237 | 1.57 | 0.01 |
| ZK3503-175.7-1 | 9.948 | 577.014 | 18984.805 | 53.050 | 1032.53 | 0.65 | 0.93 |
| ZK3503-175.7-2 | 21.114 | 216.157 | 13620.021 | 38.401 | 1555.23 | 1.59 | 0.87 |
| ZK3503-175.7-3 | 16.034 | 104.017 | 6346.182 | 22.148 | 116.41 | 1.47 | 1.18 |
| ZK3503-175.7-4 | 5.317 | 91.988 | 4948.058 | 39.393 | 303.42 | 1.29 | 0.95 |
| ZK3503-175.7-5 | 6.091 | 57.576 | 4791.258 | 8.942 | 29.53 | 0.81 | 1.18 |
| ZK3501-362.6-1 | 62.607 | 1089.103 | 9066.710 | 281.326 | 1577.00 | 1.7 | 10.2 |
| ZK3501-362.6-2 | 75.984 | 1638.878 | 7285.634 | 445.974 | 1259.92 | 1.2 | 7.94 |
| ZK3501-362.6-3 | 142.653 | 2023.462 | 3537.741 | 471.679 | 469.65 | 1.8 | 3.73 |
| ZK3501-362.6-4 | 166.662 | 2092.711 | 2998.024 | 372.120 | 940.48 | 1.6 | 1.24 |
| ZK3501-362.6-5 | 300.188 | 3263.152 | 4583.112 | 216.357 | 1660.41 | 1.7 | 1.50 |
| ZK3501-249.2-1-1 | 0.549 | 287.673 | 7708.693 | 50.518 | 37.47 | 0.19 | 0.25 |
| ZK3501-249.2-1-2 | 0.294 | 448.507 | 17884.927 | 34.613 | 94.01 | 0.25 | 1.20 |
| ZK3501-249.2-2-1 | 1.851 | 375.254 | 12422.064 | 47.943 | 78.55 | 0.38 | 0.01 |
| ZK3501-249.2-2-2 | 1.400 | 542.796 | 18991.180 | 32.422 | 129.30 | 0.50 | 1.22 |
| ZK3501-249.2-2-3 | 0.576 | 420.187 | 19435.638 | 51.690 | 431.25 | 0.35 | 0.58 |
| ZK3501-249.2-2-4 | 0.294 | 310.132 | 10022.957 | 36.752 | 60.41 | 0.16 | 0.21 |
| Area B | | | | | | | |
| 1003-502.7-3 | 29.489 | 182.070 | 18736.323 | 21.482 | 1038 | 12.2 | 1.22 |
| 1003-502.7-5 | 30.971 | 147.452 | 14936.568 | 11.392 | 520 | 12.7 | 1.04 |
| 1003-526.4-1 | 76.427 | 1009.868 | 17001.766 | 67.746 | 695 | 27.7 | 4.03 |
| 1003-526.4-2 | 75.177 | 940.291 | 20003.946 | 36.865 | 1725 | 27.3 | 4.19 |
| 1003-526.4-3 | 79.179 | 376.170 | 15861.162 | 31.810 | 681 | 25.5 | 3.37 |
| 1003-526.4-5 | 79.464 | 332.812 | 12373.200 | 19.825 | 1683 | 27.3 | 5.79 |
| ZK1003-489.8-1 | 13.508 | 203.418 | 38887.015 | 20.346 | 1555 | 2.63 | 4.53 |
| ZK1003-489.8-2 | 50.036 | 360.121 | 6920.028 | 27.795 | 8086 | 11.8 | 8.03 |
| ZK1003-489.8-4 | 26.775 | 168.499 | 29611.870 | 24.930 | 1744 | 4.22 | 5.04 |
| ZK1003-489.8-6 | 61.167 | 135.880 | 9873.583 | 23.930 | 5449 | 9.87 | 4.36 |
| 1003-524.7-1-1 | 81.035 | 64.763 | 18005.991 | 20.424 | 66.4 | 19.1 | 1.80 |
| 1003-524.7-1.2 | 114.067 | 93.214 | 15598.418 | 19.492 | 89.7 | 11.9 | 3.35 |
| 1003-524.7-2-1 | 141.352 | 462.625 | 20571.914 | 6.239 | 862 | 18.7 | 3.94 |
| 1003-524.7-1-3 | 99.669 | 22.032 | 16767.866 | 15.320 | 103 | 19.6 | 2.33 |
| 1003-524.7-1-4 | 81.794 | 88.529 | 16807.792 | 20.009 | 138 | 20.6 | 2.81 |
| 1003-524.7-2-2 | 191.395 | 84.389 | 17700.137 | 50.856 | 186 | 20.5 | 1.55 |
| 1003-524.7-2-3 | 96.638 | 233.538 | 29932.377 | 49.872 | 149 | 11.0 | 3.57 |
| 1003-524.7-2-4 | 155.736 | 81.297 | 17347.322 | 29.360 | 151 | 22.4 | 3.20 |

TABLE 2-continued

| | Ti | Al | Si | K | Mg | V | Ni |
|---|---|---|---|---|---|---|---|
| 1003-524.7-2-5 | 110.782 | 64.928 | 15155.376 | 8.267 | 109 | 14.6 | 3.87 |
| ZK1003-530.35-7 | 118.779 | 58.634 | 11841.616 | 9.001 | 93.7 | 33.9 | 4.74 |
| ZK1003-530.35-6 | 208.148 | 258.267 | 16016.726 | 102.451 | 426 | 54.7 | 33.1 |
| ZK1003-530.35-5 | 291.339 | 241.188 | 14825.374 | 95.652 | 457 | 151 | 13.2 |
| ZK1003-530.35-4 | 434.054 | 230.421 | 18728.838 | 119.517 | 512 | 170 | 7.77 |
| ZK1003-530.35-3 | 137.531 | 202.924 | 13208.296 | 55.043 | 613 | 39.8 | 3.18 |
| ZK1003-530.35-2 | 129.542 | 333.929 | 10864.143 | 40.153 | 215 | 26.5 | 3.16 |
| ZK1003-530.35-1 | 161.552 | 479.486 | 19623.906 | 70.511 | 493 | 53.2 | 4.50 |
| ZK0201-52.6-1 | 142.742 | 3385.151 | 12956.290 | 201.030 | 1534.68 | 23.9 | 4.38 |
| ZK0201-52.6-2 | 113.913 | 2445.157 | 11929.951 | 213.052 | 1128.39 | 23.9 | 6.12 |
| ZK0201-52.6-3 | 132.438 | 3659.402 | 12460.790 | 270.633 | 1110.53 | 23.1 | 4.96 |
| ZK0201-52.6-4 | 145.578 | 2539.106 | 9744.320 | 225.854 | 892.38 | 18.8 | 3.41 |
| ZK0201-52.6-5 | 87.019 | 2443.932 | 7472.444 | 133.973 | 783.09 | 12.3 | 3.80 |
| ZK0201-80.5-1-1 | 196.613 | 251.772 | 26353.736 | 27.106 | 686.98 | 21.9 | 1.28 |
| ZK0201-80.5-1-2 | 134.168 | 74.069 | 13250.259 | 33.805 | 342.23 | 22.7 | 1.38 |
| ZK0201-80.5-1-3 | 138.611 | 116.038 | 19860.015 | 34.616 | 377.23 | 22.4 | 0.98 |
| ZK0201-80.5-2-1 | 55.474 | 650.269 | 91604.327 | 67.992 | 394.86 | 31.3 | 1.16 |
| ZK0201-80.5-2-2 | 53.947 | 536.247 | 95484.701 | 73.670 | 321.25 | 36.9 | 0.69 |
| ZK0201-80.5-2-4 | 72.158 | 821.008 | 94829.251 | 96.079 | 483.12 | 51.1 | 0.01 |
| ZK0201-80.5-2-6 | 94.916 | 77.478 | 9832.123 | 13.114 | 368.77 | 11.9 | 1.23 |
| ZK0201-78.5-1 | 111.743 | 3552.786 | 31406.007 | 29.852 | 1431.76 | 41.2 | 1.45 |
| ZK0201-78.5-2 | 132.056 | 98.932 | 14833.049 | 9.759 | 277.52 | 61.3 | 1.77 |
| ZK0201-78.5-3 | 114.026 | 90.124 | 12876.603 | 12.985 | 295.44 | 44.4 | 0.91 |
| ZK0201-78.5-4 | 123.500 | 83.695 | 12115.709 | 7.482 | 217.98 | 45.7 | 1.37 |
| ZK0201-78.5-5 | 113.205 | 117.532 | 26137.298 | 20.684 | 214.99 | 42.4 | 1.25 |
| ZK0201-78.5-6 | 107.009 | 1514.220 | 49439.130 | 40.094 | 547.66 | 39.3 | 0.95 |
| ZK0301-85.9-1 | 151.195 | 1015.118 | 9440.462 | 104.574 | 175 | 19.9 | 2.45 |
| ZK0301-85.9-2 | 337.211 | 1022.708 | 11720.164 | 163.466 | 180 | 11.03 | 1.01 |
| ZK0301-85.9-3 | 254.302 | 985.037 | 11698.354 | 144.759 | 144 | 12.01 | 0.41 |
| ZK0301-85.9-4 | 428.566 | 1242.996 | 12112.610 | 179.630 | 281 | 10.09 | 0.64 |
| ZK0301-85.9-5 | 217.942 | 705.326 | 8452.651 | 111.589 | 116 | 16.01 | 1.63 |

d. Data processing: data processing is performed by using ICPMSDataCal software, including three steps of data importing, data interpretation and data screening, and average contents of major and trace elements Ti, Ni, V, K and Al+Si+Mg in the magnetite are finally obtained, denoted as c(Ti), c(Ni), c(V), c(K), and c(Al+Si+Mg). Wherein c(Ti)=48.341, c(Ni)=1.894, c(V)=1.081, c(K)=106.379, and c(Al+Si+Mg)=11930.329 in the area A. c(Ti)=133.35, c(Ni)=3.69, c(V)=30.45, c(K)=65.59, and c(Al+Si+Mg)=23217.140 in the area B.

Evaluation of the metallogenic potential of the area A:

c(Ni) is substituted into F1=−3.1484*c(Ni)+13.301 to calculate a discriminant factor F1=7.340, and when c(V)>F1, it is discriminated that the metallogenic potential is poor, and otherwise, the metallogenic potential is better;

c(V) is compared with a discriminant factor F2=2, and when c(V)>2, it is discriminated that the metallogenic potential is poor, and otherwise, the metallogenic potential is better;

c(K) is substituted into F3=0.0437*c(K)+0.4093 to calculate a discriminant factor F3=5.060, and when c(V)>F3, it is discriminated that the metallogenic potential is poor, and otherwise, the metallogenic potential is better;

c(Ti) is substituted into F4=−115.11*c(Ti)+34361 to calculate a discriminant factor F4=28791.150, and when c(Al+Si+Mg)>F4, it is discriminated that the metallogenic potential is poor, and otherwise, the metallogenic potential is better; and by comparison, when the four discriminant factors all discriminate the metallogenic potential to be better, it is determined that skarn deposits in the area A have a better metallogenic potential.

Evaluation of the metallogenic potential of the area B:

c(Ni) is substituted into F1=−3.1484*c(Ni)+13.301 to calculate a discriminant factor F1=1.675, and when c(V)>F1, it is discriminated that the metallogenic potential is poor, and otherwise, the metallogenic potential is better;

c(V) is compared with a discriminant factor F2=2, and when c(V)>2, it is discriminated that the metallogenic potential is poor, and otherwise, the metallogenic potential is better;

c(K) is substituted into F3=0.0437*c(K)+0.4093 to calculate a discriminant factor F3=3.276, and when c(V)>F3, it is discriminated that the metallogenic potential is poor, and otherwise, the metallogenic potential is better;

c(Ti) is substituted into F4=−115.11*c(Ti)+34361 to calculate a discriminant factor F4-19011.572, and when c(Al+Si+Mg)>F4, it is discriminated that the metallogenic potential is poor, and otherwise, the metallogenic potential is better; and by comparison, when the four discriminant factors all discriminate the metallogenic potential to be poor, it is determined that skarn deposits in the area B have a poor metallogenic potential.

According to the calculation results of the discriminant factors F1, F2, F3 and F4, it is discriminated that the metallogenic potential of the area A is greater than that of the area B, which is consistent with the actual field investigation results, further proving the effectiveness of the new method for evaluating the metallogenic potential based on mineral chemistry of the magnetite in the skarn deposit proposed this time.

What is claimed is:

1. A method for evaluating a metallogenic potential of a skarn deposit based on the magnetite composition, comprising:

(1) collecting geological, geophysical, geochemical, and remote sensing data in a studying area, systematically, and delineating a favorable area for mineralization;

(2) collecting magnetite-bearing samples in the favorable area for mineralization by zoning, and describing the lithology, alteration and mineralization characteristics of each sample;

(3) selecting representative magnetite samples for chemical analysis to obtain average contents of trace elements Ti, Ni, V, K and Al+Si+Mg, denoted as c(Ti), c(Ni), c(V), c(K), and c(Al+Si+Mg) in ppm; and (4) calculating a discriminant factor F1 by substituting c(Ni) into F1=−3.1484*c(Ni)+13.301, and when c(V)>F1, discriminating sections where magnetite-bearing samples are located as having a poor metallogenic potential, and otherwise, discriminating sections where magnetite-bearing samples are located as having a better metallogenic potential;

comparing c(V) with a discriminant factor F2=2, and when c(V)>2, discriminating sections where magnetite-bearing samples are located as having a poor metallogenic potential, and otherwise, discriminating sections where magnetite-bearing samples are located as having a better metallogenic potential;

calculating a discriminant factor F3 by substituting c(K) into F3=0.0437*c(K)+0.4093, and when c(V)>F3, discriminating sections where magnetite-bearing samples are located as having a poor metallogenic potential, and otherwise, discriminating sections where magnetite-bearing samples are located as having a better metallogenic potential;

calculating a discriminant factor F4 by substituting c(Ti) into F4=−115.11*c(Ti)+34361, and when c(Al+Si+Mg)>F4, discriminating sections where magnetite-bearing samples are located as having a poor metallogenic potential, and otherwise, discriminating sections where magnetite-bearing samples are located as having a better metallogenic potential; and when the four discriminant factors all discriminate the metallogenic potential to be better, determining the skarn deposit in the favorable area for mineralization to have a good metallogenic potential; and discriminating as a poor metallogenic potential in the remaining cases;

(5) carrying out deposit exploration of the skarn deposit based on a discriminant results in step 4;

wherein selecting the representative magnetite samples in the step 3 comprises:

grinding the collected samples into laser in-situ targets, observing the characteristics of magnetite corresponding to the collected samples under a microscope, recording the mineral associations and their magnetite morphology in detail, and selecting the representative magnetite samples according to results under the microscope.

2. The method according to claim 1, wherein the sample collecting process in the step 2 comprises recording a drill hole number and a drill hole depth, taking a field picture, and making a detailed field record at each sample collecting position; wherein the number of the samples is not less than five.

3. The method according to claim 1, wherein the chemical analysis in the step 3 comprises:

performing in-situ micro-area elemental analysis by using laser ablation inductively coupled plasma mass spectrometry to obtain recorded data for each analytical point.

4. The method according to claim 1, wherein the step 3 further comprises processing the recorded data obtained from the chemical analysis by using data processing software, comprising:

① Data importing, namely batch-importing elemental analysis recorded data obtained from in-situ micro-area analytical points of each magnetite sample into ICPMSDataCal software;

② Data interpretation, namely obtaining an integral curve of micro-area elements in the samples at each observation point, and adjusting the start time and the end time of the integral curve for each observation point one by one according to a principle of ensuring that a signal range of the integral curve of the selected elements is the flattest and the widest;

③ data screening, namely rejecting invalid data according to an abnormal peak of the integral curve of the elements; and ④ Data exporting, namely summarizing and batch-exporting interpreted and screened micro-area data for each single point into a file in a csv format.

5. The method according to claim 4, wherein the discriminant factors F1, F2, F3, and F4 in the step 4 are obtained by a method comprising the following steps of:

(1) collecting magnetite-bearing samples in an area where the skarn deposit is known to have a good metallogenic potential and an area where the skarn deposit is known to have a poor metallogenic potential, respectively;

(2) selecting the representative magnetite samples for chemical analysis to obtain average contents of trace elements Ti, Ni, V, K and Al+Si+Mg, denoted as c(Ti), c(Ni), c(V), c(K), and c(Al+Si+Mg) in ppm; and (3) calculating the discriminant factors performing diagram projection on data of sample collecting points with c(Ni) as an abscissa and c(V) as an ordinate, and fitting a boundary of the good metallogenic potential and the poor metallogenic potential to calculate the discriminant factor F1:F1=−3.1484*c(Ni)+13.301;

performing diagram projection on data of sample collecting points with c(Ti) as an abscissa and c(V) as an ordinate, and fitting a boundary of the good metallogenic potential and the poor metallogenic potential to calculate the discriminant factor F2: F2=2;

performing diagram projection on data of sample collecting points with c(K) as an abscissa and c(V) as an ordinate, and fitting a boundary of the good metallogenic potential and the poor metallogenic potential to calculate the discriminant factor F3: F3=0.0437*c(K)+0.4093; and performing diagram projection on data of sample collecting points with c(Ti) as an abscissa and c(Al+Si+Mg) as an ordinate, and fitting a boundary of the good metallogenic potential and the poor metallogenic potential to calculate the discriminant factor F4: F4−115.11*c(Ti)+34361.

6. The method according to claim 1, wherein the discriminant factors F1, F2, F3, and F4 in the step 4 are obtained by a method comprising the following steps of:

(1) collecting magnetite-bearing samples in an area where the skarn deposit is known to have a good metallogenic potential and an area where the skarn deposit is known to have a poor metallogenic potential, respectively;

(2) selecting the representative magnetite samples for chemical analysis to obtain average contents of trace elements Ti, Ni, V, K and Al+Si+Mg, denoted as c(Ti), c(Ni), c(V), c(K), and c(Al+Si+Mg) in ppm; and (3) calculating the discriminant factors performing diagram projection on data of sample collecting points with c(Ni) as an abscissa and c(V) as an ordinate, and fitting a boundary of the good metallogenic potential and the poor metallogenic potential to calculate the discriminant factor F1: F1=−3.1484*c(Ni)+13.301;

performing diagram projection on data of sample collecting points with c(Ti) as an abscissa and c(V) as an ordinate, and fitting a boundary of the good metallogenic potential and the poor metallogenic potential to calculate the discriminant factor F2: F2=2;

performing diagram projection on data of sample collecting points with c(K) as an abscissa and c(V) as an ordinate, and fitting a boundary of the good metallogenic potential and the poor metallogenic potential to calculate the discriminant factor F3: F3=0.0437*c(K)+0.4093; and performing diagram projection on data of sample collecting points with c(Ti) as an abscissa and c(Al+Si+Mg) as an ordinate, and fitting a boundary of the good metallogenic potential and the poor metallogenic potential to calculate the discriminant factor F4: F4=−115.11*c(Ti)+34361.

* * * * *